United States Patent [19]
Dorow et al.

[11] Patent Number: 4,522,820
[45] Date of Patent: Jun. 11, 1985

[54] TRANS-DIHYDROLISURIDE ANTIPSYCHOTIC

[75] Inventors: Rainer Dorow; Reinhard Horowski; Wolfgang Kehr; Helmut Wachtel, all of Berlin, Fed. Rep. of Germany

[73] Assignee: Schering Aktiengesellschaft, Berlin and Bergkamen, Fed. Rep. of Germany

[21] Appl. No.: 401,427

[22] Filed: Jul. 23, 1982

[30] Foreign Application Priority Data

Jul. 23, 1981 [DE] Fed. Rep. of Germany ....... 3129714

[51] Int. Cl.³ .................... A61K 31/48; A61K 31/475
[52] U.S. Cl. .................................................... 424/288
[58] Field of Search ............................... 424/261, 262

[56] References Cited

U.S. PATENT DOCUMENTS 3,954,988  5/1976  Itil et al. .

FOREIGN PATENT DOCUMENTS 2238540  2/1973  Fed. Rep. of Germany .

OTHER PUBLICATIONS

Zikan et al., Coll. Czech. Chem. Com., 25, (1960), 1922.
Psychopharmacology: A Generation of Progress, ed. Lipton et al., Raven Press, New York, 1978, 1057–1082.
"Dopamine Agonistic and Antagonistic Properties of the Ergoline Transdihydrolisuride (TDL)," 13th C.I.N.P. Congress, Jerusalem, 20.–25.6.1982.
Chem. Abstracts, vol. 78–24018y and 24231n, (1973).

Primary Examiner—Stanley J. Friedman
Attorney, Agent, or Firm—Millen & White

[57] ABSTRACT

The treatment of psychosis with N-(D-6-methyl-8-iso-ergolin)-N'N-diethylurea.

9 Claims, No Drawings

TRANS-DIHYDROLISURIDE ANTIPSYCHOTIC

BACKGROUND OF THE INVENTION

The present invention relates to a new use for N-(D-6-methyl-8-isoergolinyl)-N'N-diethylurea (=trans-dihydrolisuride) and its physiologically compatible salts, and the corresponding medicinal agents.

The compound trans-dihydrolisuride proper and its nidation- and lactation-inhibiting effect when orally administered to animals are known (see, e.g., German Pat. No. 2,238,540).

It is also known that ergoline derivatives, such as lisuride hydrogen maleate (Zikan et al., Coll. Czech. Chem. Commun. 25 : 19, 22 [1960]) possess neuropsychotropic properties (DOS No. 2,359,128).

Also conventional are neuroleptics such as haloperidol and chlorpromazine, used for the symptomatic treatment of schizophrenic psychoses. However, the known neuroleoptics have the disadvantage of causing counter-regulatory stimulation of dopamine synthesis in the nigrostriatal system, due to their blockage effect on postsynaptic dopamine receptors, triggering undesirable extra-pyramidal-motoric side effects. Undesirable permanent effects of chronic treatment of schizophrenic psychoses with neuroleptics, such as tardive dyskinesia, can likewise be traced back to the long-term blockage of dopamine receptors.

SUMMARY OF THE INVENTION

It is an object of the present invention to provide a medicament overcoming these disadvantages and a corresponding method of treating psychoses.

Upon further study of the specification and appended claims, further objects and advantages of this invention will become apparent to those skilled in the art.

These objects have been attained by providing a method of treating psychoses in a patient suffering from psychoses comprising administering an antipsychotically effective amount of N-(D-6-methyl-8-isoergolinyl)-N'N-diethylurea or a physiologically acceptable salt thereof to the patient.

DETAILED DISCUSSION

In art accepted pharmacological studies on animals, it has been discovered that trans-dihydrolisuride, besides having generally CNS-depressive effects, stimulates dopamine synthesis in the corpus striatum of small rodents, in dependence of the dosage, only to an extent of up to 60% of the values attainable by haloperidol. In low dosages, trans-dihydrolisuride showed an inhibitory effect on dopamine synthesis, determined by the method developed by KEHR (W. Kehr, Naunyn-Schmiedeberg Arch. Pharmacol. 274, 273 [1972]).

The conditioned avoidance reaction in rats in interchangeable cages was inhibited by trans-dihydrolisuride without impairment of unconditioned flight reflex (method modified according to Niemegeers, C. J. E. et al., Psychopharmacologia 16 : 161 [1969]).

Furthermore, trans-dihydrolisuride exhibits apomorphine-antagonistic effects in the modified model of Ther (Ther, L. and Schramm, A., Arch, Int. Pharmacodyn. Ther. 138, 302 [1962]), as well as catalepsy-triggering effects (modified according to Timsit, J., Therapie 22 : 885 [1967]). In small rodents, trans-dihydrolisuride showed an efficacy reduced by about one-half compared with that of haloperidol with respect to catalepsy, a behavioral symptom correlated in man with extrapyramidalmotoric side effects as well as with respect to apomorphine antagonism, correlated in man with the desired dopamine receptor blockage.

The results of these art accepted pharmacological studies on animals admit the final conclusion that trans-dihydrolisuride possesses dopamine-receptor-blocking properties in conjunction with a residual dopamine-agonistic activity. As a consequence thereof, there is no occurrence of extrapyramidal-motoric accompanying and tardive effects in a treatment with trans-dihydrolisuride, with the same, desired high level of efficacy.

Corresponding pharmacological clinical studies on human subjects confirmed the conclusion drawn from the findings obtained in the animal experiments, and demonstrated that trans-dihydrolisuride, after a single oral administration in a dosage range of 0.2–1.0 mg, shows effective properties comparable to chlorpromazine as the standard neuroleptic, but substantially less pronounced side effects such as fatigue, stupor, and weakness of concentration, as well as less pronounced peripheral alpha-adrenolytic side effects. See also Example 1 below.

Trans-dihydrolisuride furthermore shows, in this and other studies, even in a relatively low dosage range, a prolactin-lowering activity which, as compared with the findings derivable from animal experiments, is markedly stronger and of long duration. This distinguishes trans-dihydrolisuride advantageously over all other clinically used neuroleptics, for example for the treatment of schizophrenia or for sedation, for example, also of aged patients, since all of these neuroleptics show a prolactin-raising effect. The latter effect is the cause of numerous side effects, such as cycle disturbances and galactorrhea in females as well as disturbances of potency and libido in males.

Consequently, trans-dihydrolisuride is an agent for the symptomatic treatment of psychoses in patients, e.g., in humans and is distinguished by low side effects due to its novel mechanism of activity. Accordingly, trans-dihydrolisuride is suitable for monotherapy of acute and chronic diseases of the schizophrenic array of disturbances, as well as for complementary usage in patients who suffer, under treatment with neuroleptics, interfering effects on the side of the extrapyramidal-motoric systems, or disturbances in cycle, potency, and libido. Typical psychotic or schizophrenic conditions and symptoms are well-known and recognizable to the expert, e.g., as indicating antipsychotic treatment, and are disclosed, e.g., in PSYCHOPHARMACOLOGY: A Generation of Progress, edited by M. A. Lipton, A. DiMascio and K. F. Killam, Raven Press, N.Y. 1978, and Comprehensive Textbook of Psychiatry, edited by A. M. Freedom and H. I. Kaplan, Williams & Wilkins Co., Baltimore 1974, whose disclosures are incorporated by reference herein.

In medical practice, medicaments comprising trans-dihydrolisuride can be administered subcutaneously, intramuscularly, intravenously, and above all orally.

Physiologically compatible salts for use in these medicaments include salts of trans-dihydrolisuride with inorganic and organic acids. Suitable for salt formation, for example, are included hydrochloric acid, phosphoric acid, sulfuric acid, methanesulfonic acid, glucoheptanoic acid, succinic acid, tartaric maleic acid, etc. A preferred salt is transdihydrolisuride dihydrogen phosphate.

The daily dosage of the compound of this invention is 0.1–5.0 mg, but preferably 0.2–1.5 mg. The dosage can be administered singly or in several administrations. The agents of this invention are also suitable for long-term treatment since no psychic dependency is created, e.g., for periods of 3 months up to 30 years. The drug specialties can be prepared in a manner known per se by processing trans-dihydrolisuride with the vehicles, diluents, flavor-ameliorating agents, etc., customary in galenic pharmacy.

Especially suitable for injections are aqueous solutions, but also oily solutions as well as suspensions.

To prepare intramuscular depot forms, the active agents can be suspended or dissolved in fatty oils by following conventional methods. Such depot forms contain about 0.5–5.0 mg of active agent per administration unit; the active agent is released over a period of 1–10 days.

The medicinal agents of this invention are suitable for oral administration especially in the form of tablets, capsules, dragees, pills, suspensions, and solutions. The amount of active ingredient per oral administration unit is usually 0.1–1.0 mg, preferably 0.5 mg. Also suitable are oral timed release formulations, obtained in the usual way, for example by adding hydrogenated fats and by processing with resinogenous substances and lacquers. Drops for oral administration can be prepared as aqueous solutions or suspensions of the active agent in oils with the addition of flavor-ameliorating agents and/or solubilizers. One daily dosage of 3×10 drops can contain, for example, 0.2–1.5 mg.

Unless indicated otherwise herein, the use of trans-dihydrolisuride in accordance with this invention is analogous to the administration of, e.g., the well-known anti-psychotics THORAZINE ® and HALDOL ®.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

In clinical studies, inter alia, 15 healthy test subjects received, in a randomized, double-blind crossover arrangement, a single oral administration, in intervals of 7 days, of a placebo, 75 mg of chlorpromazine, 0.2 mg, 0.5 mg, or 1.0 mg of transdihydrolisuride. Effects and side effects were determined using electrophysiological and psycho-experimental parameters, as well as self-evaluation records and records of physicians' findings, and analyzed biostatistically (method according to Herrmann et al., Pharmakopsychiat. 12 : 19 [1979]). The investigation showed signs of inhibition of CNS functions by trans-dihydrolisuride similar in quality to chlorpromazine, but less pronounced quantitatively due to the dopamine-partial-agonistic effect.

EXAMPLE 2

2.0 mg. of N-(D-6-methyl-8-isoergolinyl)-N,N'-diethylurea are mixed homogeneously with 110.5 mg. of lactose, 57.5 mg. of corn starch, 2.0 mg. of "Aerosil", 2.5 mg. of polyvinylpyrrolidone 25, and 0.5 mg. of magnesium stearate and compressed, without previous granulation, into round, biplanar tablets with a breaking notch and a final weight of 175 mg.

EXAMPLE 3

To produce an injection solution, 1.0 mg. of micronized N-(D-6-methyl-8-isoergolinyl)-N,N'-diethylurea is suspended in 618.6 mg. of benzyl benzoate (USP XVII) and 353.4 mg. of caster oil (USP XVII); the suspension is sterilized and filled aseptically into 3-ml. ampoules.

EXAMPLE 4

Respectively 1.0 mg of N-(D-6-methyl-8-isoergolinyl)-N,N'-diethylurea (micronized, particle size 2-8μ) is mixed homogeneously with 150 mg. of lactose (USP XVII) and filled into hard-gelatin capsules (5×15 mm).

EXAMPLE 5

To produce an aqueous injection solution, 1.0 mg of N-(D-6-methyl-8-isoergolinyl)-N,N'-diethylurea is suspended in 1.0 ml of bidistelled water, and the suspension is aseptically filled into 2-ml. ampoules.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method of treating psychosis in a patient suffering from psychosis comprising administering an antipsychotically effective amount of N-(D-6-methyl-8-isoergolinyl)-N'N-diethylurea or a physiologically acceptable salt thereof to the patient.

2. A method of claim 1 wherein the administration is oral.

3. A method of claim 1 wherein the administration is subcutaneously, intramuscularly or intravenously.

4. A method of claim 1 or 2 wherein the daily dosage is 0.1 to 5.0 mg.

5. A method of claim 4 wherein the daily dosage is 0.2 to 1.5 mg.

6. A method of claim 1 wherein the administration is long term.

7. A method of claim 1 wherein the patient is not suffering from an indication treatable by nidation or lactation inhibition.

8. A method of claim 1 or 2 wherein the patient is suffering from schizophrenia.

9. A method of claim 1 or 2 wherein the antipsychotic agent is the dihydrogen phosphate salt of N-(D-6-methyl-8-isoergolinyl)-N'N-diethylurea.